(12) United States Patent
Torikai

(10) Patent No.: US 10,160,694 B2
(45) Date of Patent: Dec. 25, 2018

(54) AGENT FOR INTRODUCING PROTECTING GROUP FOR HYDROXY GROUP AND/OR MERCAPTO GROUP

(71) Applicant: KYUSHU UNIVERSITY, NATIONAL UNIVERSITY CORPORATION, Fukuoka (JP)

(72) Inventor: Kohei Torikai, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 15/517,899

(22) PCT Filed: Sep. 30, 2015

(86) PCT No.: PCT/JP2015/077835
§ 371 (c)(1),
(2) Date: Apr. 7, 2017

(87) PCT Pub. No.: WO2016/056448
PCT Pub. Date: Apr. 14, 2016

(65) Prior Publication Data
US 2017/0305809 A1  Oct. 26, 2017

(30) Foreign Application Priority Data

Oct. 7, 2014  (JP) ................ 2014-206408

(51) Int. Cl.
| | | |
|---|---|---|
| *C07C 41/16* | (2006.01) | |
| *C07B 41/02* | (2006.01) | |
| *C07C 43/164* | (2006.01) | |
| *C07C 43/174* | (2006.01) | |
| *C07B 51/00* | (2006.01) | |
| *C07C 309/63* | (2006.01) | |
| *C07C 15/14* | (2006.01) | |
| *C07C 22/04* | (2006.01) | |
| *C07D 209/04* | (2006.01) | |
| *C07D 215/02* | (2006.01) | |
| *C07D 333/72* | (2006.01) | |

(52) U.S. Cl.
CPC ............ *C07B 41/02* (2013.01); *C07B 51/00* (2013.01); *C07C 15/14* (2013.01); *C07C 22/04* (2013.01); *C07C 41/16* (2013.01); *C07C 43/164* (2013.01); *C07C 43/174* (2013.01); *C07C 309/63* (2013.01); *C07D 209/04* (2013.01); *C07D 215/02* (2013.01); *C07D 333/72* (2013.01); *Y02P 20/55* (2015.11)

(58) Field of Classification Search
CPC ....................................................... C07B 41/02
See application file for complete search history.

(56) References Cited

PUBLICATIONS

Stefan et al., Org. Letters., 14(13), 2012, pp. 3490-3493.*
Gomez et al., Tetrahedron , 62(42), 2006, pp. 9832-9839.*
Gathirwa et al.: "Benzylation of hydroxyl groups with tertiary anime as a base," Nagasaki University, Elsevier Ltd., Tetrahedron 68, pp. 370-375, Nov. 14, 2011.
Iverson et al., "Benzyl Trichloroacetimidate, a Versatile Reagent for Acid-catalysed Benzylation of Hydroxy-groups," National Research Council of Canada, J.C.S. Chem Comm, pp. 1240-1241, Sep. 1981.
Kozikowski et al: "Protection of Alcohols as their p-Methoxybenzyloxy Methal Ethers," University of Pittsburgh, Pergamon Journals Ltd., vol. 28, No. 43, pp. 5128-5128, 1987.
Stefan et al, Stereoselective Synthesis of the C9-C19 Fragment of Lyngbyaloside B and C via Ether Transfer, Organic Letters, vol. 14, No. 13, p. 3490-3493, 2012.
Rajaram et al., "Reductions using LiCl/NaBH$_4$: A rapid and efficient cleavage of organic disulfides to mercaptans" Indian Institute of Chemical Technology, Indian Journal of Chemistry, vol. 40B, pp. 622-624, Jul. 2001.
Gomez et al: "[1,2]-Witting rearrangement from chloromethyl ethers," Tetrahedron, Elsevier Science Publishers, Vo. 62, No. 42, ISSN: 0040-4020, DOI 10.1016/J.TET.2006.08.028, pp. 9832-9839, Oct. 16, 2006.
Extended Search Report issued in European Patent Application No. 15848889.0, dated Feb. 20, 2018.

* cited by examiner

*Primary Examiner* — Paul V Ward
(74) *Attorney, Agent, or Firm* — Michael Best & Friedrich LLP

(57) ABSTRACT

A novel agent for introducing a protecting group for a hydroxy group and/or a mercapto group that can be introduced and removed under mild conditions is provided. The agent for introducing a protecting group for a hydroxy group and/or mercapto group of a substrate compound having the hydroxy group and/or mercapto group is represented by the following formula (I), wherein A represents a ring structure having 1 to 5 rings in which two carbon atoms of an adjacent benzene ring are included, the ring structure comprises a substituted or unsubstituted five-membered ring or six-membered ring and optionally include a heterocycle; each of $R^1$, $R^2$, $R^3$, and $R^4$ is independently a hydrogen atom or a linear or branched alkyl group having 1 to 5 carbon atoms; and X is a halogen atom or $OSO_2R^5$ ($R^5$=an aryl group or an alkyl group).

16 Claims, No Drawings

AGENT FOR INTRODUCING PROTECTING GROUP FOR HYDROXY GROUP AND/OR MERCAPTO GROUP

TECHNICAL FIELD

The present invention relates to an agent for introducing a protecting group for a hydroxy group and/or a mercapto group and particularly to a novel agent for introducing a protecting group for a hydroxy group and/or a mercapto group that can be introduced and removed under mild conditions.

BACKGROUND ART

A benzyl (Bn) group and substitution products thereof have been utilized as protecting groups in the field of organic synthetic chemistry for a long time (for example, see Non Patent Literature 1). The biggest advantage of Bn-based protecting groups is that they can be easily and cleanly removed by hydrogenolysis (for example, $H_2$ and Pd/C). Especially a p-methoxybenzyl (PMB) group and a 2-naphthylmethyl (NAP) group can be easily removed with an oxidant such as dichlorodicyanobenzoquinone (DDQ) or ammonium cerium nitrate (CAN) and therefore are excellent in that they can be removed separately from a Bn group (for example, see Non Patent Literature 1).

While removal is easy, strongly basic (for example, NaH, BnBr, and DMF, or DIPEA, BnBr, neat, and 150° C. (for example, see Non Patent Literature 2)) or strongly acidic (for example, BnOC(NH)CCl$_3$ and TfOH) (for example, see Non Patent Literature 3) conditions are usually needed for the introduction of a Bn-based protecting group (a large number of examples using Lewis acids are also known)$_T$. These conventional methods are also problematic in that they are hard to be applied to a small scale experiment and to be conducted by a person who are not trained as a synthetic organic chemist, because all of these reactions are moisture-sensitive. For protecting an alcohol unstable to acids and bases, benzyloxymethyl (BOM) groups, which can be introduced in the presence of a weaker base, diisopropylethylamine (DIPEA) are generally utilized. So far, as an oxidatively removable protecting group in the later stage of multistep synthesis, a p-methoxybenzyloxymethyl (PMBOM) group has been used (for example, see Non Patent Literature 1).

CITATION LIST

Non Patent Literature

Non Patent Literature 1: Wuts, P. G. M.; Greene, T. W. Greene's Protective Groups in Organic Synthesis, 4th ed.; John Wiley & Sons: New Jersey, 2007.
Non Patent Literature 2: Gathirwa, J. W.; Maki, T. Tetrahedron 2012, 68, 370-375.
Non Patent Literature 3: Iversen, T.; Bundle, K. R. J. Chem. Soc., Chem. Commun. 1981, 1240-1241.
Non Patent Literature 4: Kozikowski, A. P.; Wu, J.-P. Tetrahedron Lett. 1987, 28, 5125-5128.
Non Patent Literature 5: Stefan, E.; Taylor, R. E. Org. Lett. 2012, 14, 3490-3493.
Non Patent Literature 6: LiCl, NaBH4, THF. See: Rajaram, S.; Chary, K. P.; Iyengar, D. S. Indian J. Chem., Sect. B: Org. Chem. Incl. Med. Chem. 2001, 40B, 622-624.

SUMMARY OF INVENTION

Technical Problem

However, it has been known that PMBOMCl used for the introduction of a PMBOM group cannot be stored at −20° C. even for 3 days (see Non Patent Literature 4), and PMBOMCl needs to be freshly prepared when it is used. Further, it is necessary for the preparation of PMBOMCl to be conducted at low temperature (−78° C.), which is unsuitable for large scale synthesis in a company or the like. At the same time, this reaction produces a sulfur-containing compound as a by-product, and therefore there is a possibility that, the sulfur-containing compound acts as a catalyst poison to inhibit the hydrogenolysis for subsequent deprotection. This possibility is also supported by the fact that the hydrogenolysis of a PMBOM ether just after preparation, often results in failure. Moreover, the introduction reaction using DIPEA cannot be universal nor applied to all the cases, e.g., application to a 2-acetoxy-1-ol system is difficult because acyl migration as well as other side reactions undergo.

In order to solve all the above-described problems, the present invention provides a novel protecting group for a hydroxy group and/or a mercapto group (for example, a novel BOM-based protecting group-introducing agent) that allows introduction and removal under mild conditions.

Solution to Problem

As a result of diligent study, the present inventor has found that when a certain compound having an arylmethoxymethyl group is used as an agent for introducing a protecting group for a hydroxy group and/or a mercapto group, it allows introduction under milder conditions than conventional ones, and further that the compound also has high storage properties.

Specifically, an agent for introducing a protecting group for a hydroxy group and/or a mercapto group according to the present invention is an agent for introducing a protecting group to a hydroxy group and/or mercapto group of a substrate compound having the hydroxy group and/or mercapto group, and is represented by the following formula (I):

[Formula 1]

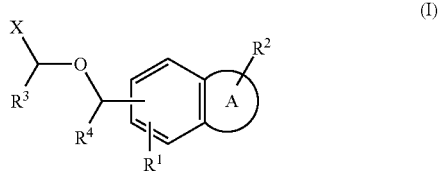

(I)

wherein A represents a ring structure having 1 to 5 rings in which two carbon atoms of an adjacent benzene ring are included, the ring structure comprises a substituted or unsubstituted five-membered ring or six-membered ring and optionally include a heterocycle; each of $R^1$, $R^2$, $R^3$, and $R^4$ is independently a hydrogen atom or a linear or branched alkyl group having 1 to 5 carbon atoms; and X is a halogen atom or $OSO_2R^5$ ($R^5$=an aryl group or an alkyl group).

DESCRIPTION OF EMBODIMENT

The agent for introducing a protecting group for a hydroxy group and/or a mercapto group according to the present invention is represented by the above-described formula (I).

In the above formula, A is not particularly limited as long as it satisfies the above-described ring structure. For example, A can contain a benzene ring, a pyridine ring, a thiophene ring, a pyrrole ring, a naphthalene ring, or an anthracene ring as shown in the following formula (I)-1 to formula (I)-6:

[Formula 2]

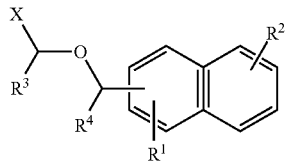
(I)-1

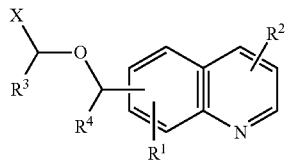
(I)-2

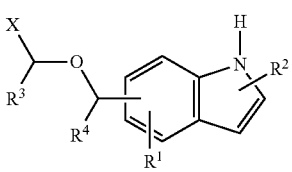
(I)-3

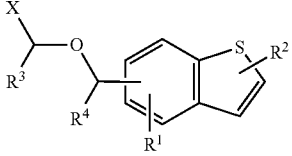
(I)-4

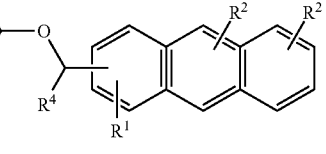
(I)-5 wherein each of two $R^2$ independently represent either a hydrogen atom or a linear or branched alkyl group having 1 to 5 carbon atoms.

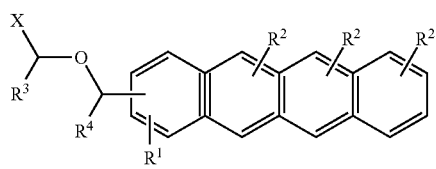
(I)-6 wherein each of three $R^2$ independently represent either a hydrogen atom or a linear or branched alkyl group having 1 to 5 carbon atoms.

With any of the compounds represented by the above-described formulas (I)-1 to (I)-6, the desired reaction for introducing a protecting group proceeds. However, synthesis is easy when A is a ring having a smaller molecular size, and therefore it is preferred that A is a single ring. Specifically, it is preferred that A is a benzene ring, a pyridine ring, a thiophene ring, or a pyrrole ring. Among these, because of easy availability and ease of handling, a compound in which A comprises a benzene ring is preferably used. In addition, A may be substituted by a substituent represented by the above $R^2$, but an unsubstituted compound, that is, a compound in which $R^2$ is hydrogen, is preferred because of easy availability and ease of handling. Because of the above, examples of preferred compounds include the naphthylmethoxymethyl (NAPOM) derivative shown below:

[Formula 3]

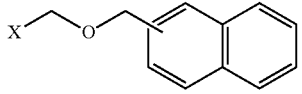
(I)-a

The naphthylmethoxymethyl (NAPOM) derivative represented by the above-described formula (I)-a may be a 1-naphthylmethoxymethyl (NAPOM) derivative or a 2-naphthylmethoxymethyl (NAPOM) derivative as represented by the following formula (I)-a' or formula (I)-a", regardless of the bonding position of the methoxymethyl group to the naphthyl group (position 1 or position 2).

[Formula 4]

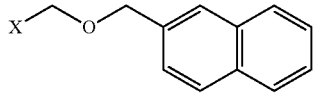
(I)-a'

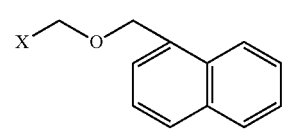
(I)-a"

X is not particularly limited as long as it is a halogen atom or $OSO_2R^5$ ($R^5$=an aryl group or an alkyl group). Because good reactivity is easily obtained, X is preferably a halogen atom. Because of easy availability and ease of handling, a compound in which X is a chlorine atom or a bromine atom as represented by the following formula (I)-a-1 to formula (I)-a-2 is preferably used as the naphthylmethoxymethyl (NAPOM) derivative, and particularly, because of the high storage stability of the NAPOM group-introducing agent, a compound in which X is a chlorine atom (that is, naphthylmethoxymethyl (NAPOM) chloride) is preferred.

[Formula 5]

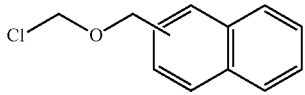
(I)-a-1

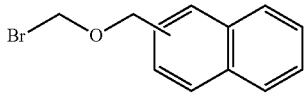
(I)-a-2

X may be a halogen element other than the above, and, for example, when a naphthylmethoxymethyl (NAPOM)

derivative in which X is fluorine or iodine as represented by the following formula (I)-a-3 to formula (I)-a-4 is used, the desired reaction can be allowed to proceed.

[Formula 6]

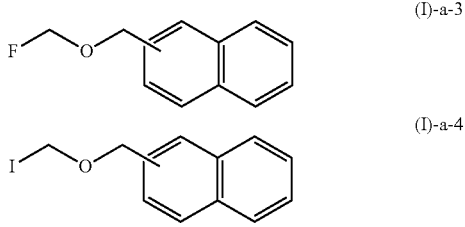

(I)-a-3

(I)-a-4

The present inventor has found the compound represented by the above general formula (I) as a novel protecting group for a hydroxy group and/or a mercapto group according to this embodiment, especially the naphthylmethoxymethyl (NAPOM) derivative as a particularly preferred one, and confirmed that it exhibits excellent reactivity as a protecting group (see Examples described later). The detailed reason why such an excellent property is exhibited is not clarified yet but is presumed to be that the electronic state formed by the arylmethoxymethyl group is optimal for allowing introduction and removal reactions for a hydroxy group and/or a mercapto group and storage.

Particularly with the NAPOM derivative, a reaction is successfully achieved to introduce a protecting group under room temperature and extremely mild conditions, for example, even an unstable alcohol that usually easily undergoes acyl migration, such as 2-acetoxy-1-ol, can be protected therewith in a high yield.

Further, in a reaction with the protecting group for a hydroxy group and/or a mercapto group according to this embodiment, said substrate compounds are preferably reacted with the compound represented by the above formula (I) in the coexistence of a base. As such a base, one generally used as a base can be used. Although not particularly limited, a base represented by the following formula (II)-1 or formula (II)-2 is more preferably added, and further, the base represented by formula (II)-1 is particularly preferably added, in view of easily obtaining the target NAPOM derivative in a high yield while hardly causing undesired isomerization.

[Formula 7]

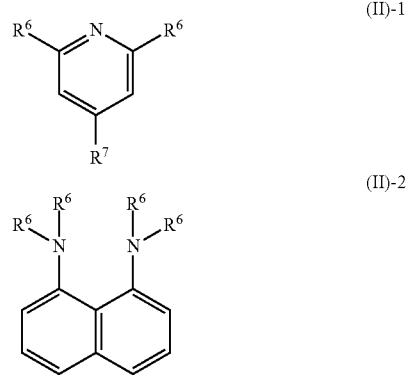

(II)-1

(II)-2 wherein each of $R^6$ and $R^7$ is independently a hydrogen atom or a linear or branched alkyl group having 1 to 5 carbon atoms.

Examples of the base represented by the above formula (II)-1 include 2,6-lutidine, 2,6-di-tert-butyl-4-methylpyridine (DTBMP), and 2,4,6-trimethylpyridine (collidine) shown below. Because of easy availability, 2,6-lutidine and 2,6-di-tert-butyl-4-methylpyridine (DTBMP) are preferably used.

[Formula 8]

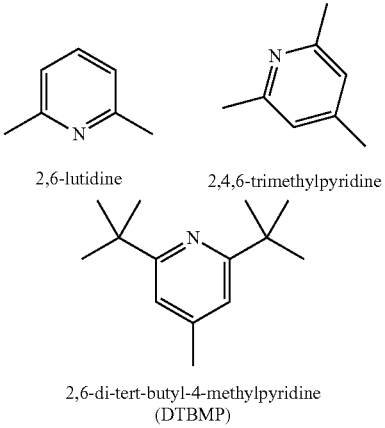

2,6-lutidine   2,4,6-trimethylpyridine 2,6-di-tert-butyl-4-methylpyridine (DTBMP)

Examples of the base represented by the above formula (II)-2 include 1,8-bis(dimethylamino)naphthalene (the so-called proton sponge) shown below:

[Formula 9]

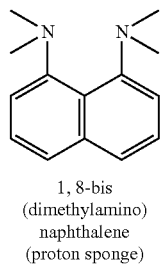

1, 8-bis (dimethylamino) naphthalene (proton sponge)

As described above, in this embodiment, even when 2-acetoxy-1-ol is used as a substrate, using 2,6-lutidine or DTBMP as a preferred base can provide the target NAPOM-protected form in a high yield while undesired isomerization is hardly caused. In contrast to this, when a conventional tertiary amine, such as diisopropylethylamine (DIPEA), is applied to the conversion of 2-acetoxy-1-ol into a NAPOM-protected form, undesired isomerization occurs. Also in this context, the excellent effect of obtaining the NAPOM-protected form in a high yield is exhibited by suppressing a side reaction through mild conditions that cannot be conventionally realized. Of course, also in this embodiment, it is also naturally possible to use a conventional tertiary amine such as diisopropylethylamine (DIPEA).

On the other hand, the NAPOM group can be easily removed by using an oxidant such as DDQ or CAN. These features and the fact that NAPOMCl, which is an introducing agent, can be stored for a long period indicate that the NAPOM group can be recognized as a protecting group more easily used than existing PMB and PMBOM groups.

TABLE 1
Introduction and Removal of NAPOM groups onto hydroxy and mercapto groups
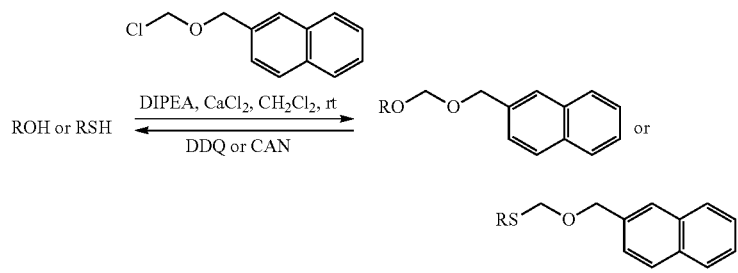
| Entry | Substrate | Yield/%[a] | |
|---|---|---|---|
| | | Introduction[b] | Removal[c] |
| 1 | 1a: R = H<br>1b: R = NAPOM | 91 | 98 |
| 2 | 2a: R = H<br>2b: R = NAPOM | 90 | 96 |
| 3 | 3a: R = H<br>3b: R = NAPOM | 96 | 91 |
| 4 | 4a: R = H<br>4b: R = NAPOM | 94 | 88 |
| 5 | 5a: R = H<br>5b: R = NAPOM | 91[d] | Quant.[e] |

TABLE 1-continued

Introduction and Removal of NAPOM groups onto hydroxy and mercapto groups

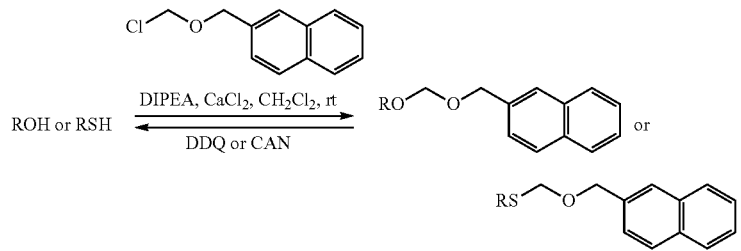

| | | Yield/%[a] | |
|---|---|---|---|
| Entry | Substrate | Introduction[b] | Removal[c] |
| 6 | 6a: R = H<br>6b: R = NAPOM<br>6c: R = SCH$_2$CH$_2$Ph | 88 | 6c: 94 |

[a]Isolated yields, basically after silica gel column chromatography.
[b]NAPOMCl (1.8 to 3 eq.), DIPEA (4 to 6 eq.), CaCl$_2$ (100 wt %), CH$_2$Cl$_2$ (subs. conc. 0.1 M), rt, 6.5 to 32.5 h.
[c]DDQ (1.5 eq.), CH$_2$Cl$_2$/phosphate buffered water (pH 7.0) = 18/1, rt, 2 to 3.5 h.
[d]Purified by recrystallization.
[e]DDQ (2.0 eq.), CH$_2$Cl$_2$/pH 7.0 buffer, rt, 22.5 h.

Introduction and Removal of NAPOM groups onto hydroxy and mercapto groups

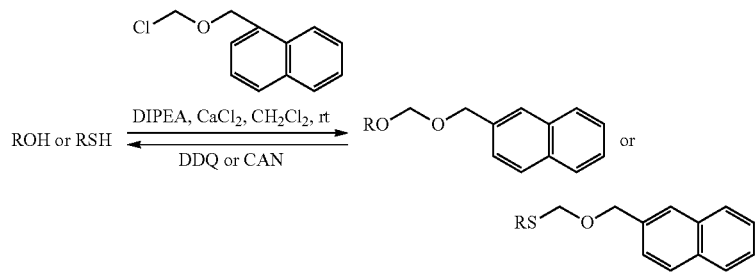

| | | Yield/%[a] | |
|---|---|---|---|
| Entry | Substrate | Introduction[b] | Removal[c] |
| 1 | 1a: R = H<br>1c: R = 1-NAPOM | Quant. | 64 |
| 2 | 2a: R = H<br>2c: R = 1-NAPOM | 90 | 86 |

Introduction and Removal of NAPOM groups onto hydroxy and mercapto groups

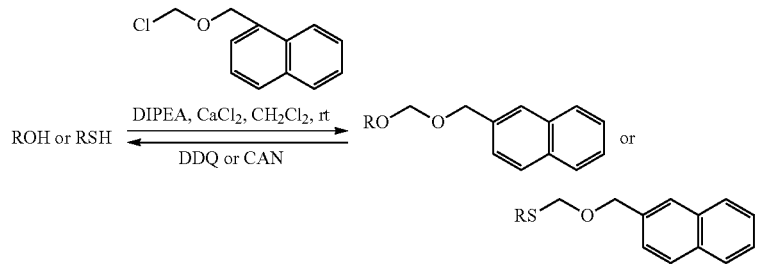

| | | Yield/%[a] | |
|---|---|---|---|
| Entry | Substrate | Introduction[b] | Removal[c] |
| 3 | 3a: R = H<br>3c: R = 1-NAPOM (phenethyl-C(CH₃)₂-OR) | 96 | 99 |

[a]Isolated yields, basically after silica gel column chromatography.
[b]NAPOMCl (1.8 to 3 eq.), DIPEA (4 to 6 eq.), CaCl₂ (100 wt %), CH₂Cl₂ (subs. conc. 0.1 M), rt, 6.5 to 32.5 h.
[c]DDQ (1.5 eq.), CH₂Cl₂/phosphate buffered water (pH 7.0) = 18/1, rt, 2 to 3.5 h.
[d]Purified by recrystallization.

First, the preparation of NAPOMCl was attempted according to a method known from a literature (see Non Patent Literature 5). When HCl gas was passed through a mixture of 2-naphthylmethyl alcohol and paraformaldehyde, high yield and highly pure NAPOMCl was obtained, and the obtained NAPOMCl could be stably stored in the coexistence of CaCl₂ at −20° C. for 8 months or more (NAPOMCl cannot be stored at room temperature (half-life about 2 weeks) but can be stored at 4° C. for several months (when NAPOMCl is stored at 4° C. for 1 month, 13% is lost.). Then, in this embodiment, protection and deprotection with a NAPOM group was studied for various substrates having hydroxy and mercapto groups (Table 1).

When NAPOMCl was allowed to act on each of primary (1a), secondary (2a), and tertiary (3a) alcohols, a carboxylic acid 4a, and a phenol 5a in the coexistence of DIPEA and CaCl₂, the desired NAPOM form was provided in a good yield in each case (>90%, Entries 1-5).

In the case of the tertiary alcohol 3a in which the reaction site was bulky, excessive reactants (3 equivalents of NAPOMCl and 6 equivalents of DIPEA) and the prolonged reaction time (32.5 h) were required for the completion of the reaction, but the desired product was obtained at room temperature without specially causing a big problem. In addition, also regarding a thiol 6a, a NAPOM-protected form 6b was similarly synthesized (88%, Entry 6).

Next, in this embodiment, the removal of the NAPOM group was studied. When DDQ was allowed to act on each of NAPOM-protected forms 1b-5b in a mixed solvent of dichloromethane and pH 7 phosphate buffer solution (18:1) at room temperature, the reactions proceeded rapidly, and the desired deprotected forms were quantitatively obtained in a yield of 88% (Entries 1-5).

On the other hand, it was found that when DDQ was allowed to act on the NAPOM sulfide 6b, a disulfide 6c was obtained in a yield of 94%, which was made under oxidative conditions from each of the thiol 6a which was yielded by the removal of the NAPOM group. (Entry 6. The conversion of the disulfide (6c) into the thiol (6a) is known from a literature (see Non Patent Literature 6)). These results indicate that the NAPOM group can be a novel BOM-based protecting group that can be removed under oxidative conditions.

TABLE 2

Table 2. Introduction and Removal of NAPOM Group on Sensitive Alcohols

| | | | | Yield/% | |
|---|---|---|---|---|---|
| Entry | Substrate | Reagents | Product | a | b |
| 1 | 7 (PhCH(OAc)CH₂OH) | NAPOMCl<br>DIPEA | 8a: R¹ = Ac, R² = NAPOM<br>8b: R¹ = NAPOM, R² = Ac | 47[a] | 17[a] |

TABLE 2-continued

Table 2. Introduction and Removal of NAPOM Group on Sensitive Alcohols

| Entry | Substrate | Reagents | Product | Yield/% a | b |
|---|---|---|---|---|---|
| 2 | 7 | NAPOMCI, TBAI, 2,6-lutidine | 8a, 8b | 89 | 3 |
| 3 | 4-(chloromethyl)benzyl alcohol (9) | NAPOMCI, 2,6-lutidine | NAPOM ether 10a | 75 | |
| 4 | 1-phenyl-2-(ONAPOM)ethanol (11) | DDQ, pH 7.0 buffer | 1-phenyl-1,2-ethanediol 12a (2-naphthyl); cyclic acetal 12b | 27 | 51 |
| 5 | 11 | DDQ, H₂O; then MeOH | 12a, 12b | 90 | N.D. |

$^a$Inseparable. Yield was calculated from $^1$H-NMR spectrum of the mixture.

Next, in this embodiment, the introduction of a NAPOM group into an unstable substrate was carried out. 1,2-Diols often exhibit unpredictable behavior in protection and deprotection. Especially a system, in which one hydroxy group of a 1,2-diol has an acyl group, is known to easily undergo acyl migration and isomerize under acidic and basic conditions. In fact, as far as the applicant knows, there has been no case in which a BOM group or a MOM group was introduced into a 2-acyloxy-1-ol system without causing isomerization. Therefore, first, an attempt was made to introduce a NAPOM group into 2-acetoxy-1-ol 7 by a conventional method using DIPEA (Entry 1 in table 2).

As a result, even with such weak basicity of the DIPEA and at relatively moderate room temperature, acyl migration proceeded as feared at first, and a mixture of the desired protected form 8a (47%) and a rearrangement reaction product 8b (19%) was obtained (the reaction was not clean, and the mass balance was also poor).

Therefore, various reaction conditions were studied (for example, when DMAP was used as a base, acyl migration proceeded). As a result, by using 2,6-lutidine and tetrabutylammonium iodide (TBAI) instead of DIPEA (Entry 2), the acyl migration was suppressed to 3%, and the desired 8a was successfully obtained in a yield of 89%. This method could be also applied to the conversion of an alcohol 9 into a NAPOM form (Entry 3, 75%), to which alcohol 9 an alkylation method using Ag₂O could not be applied because the alcohol 9 had a chloro group having high reactivity.

Next, the problem in the deprotection of the mono-NAPOM form of a 1,2-diol 11 was addressed (Entry 4). When DDQ was first allowed to act on 11 in a pH 7 buffer solution according to a conventional method, a cyclic acetal 12b was the main product (51%), and only 27% of the desired diol 12a was obtained. Then, in an attempt to acid-hydrolyze 12b in the system to derive 12a, the reaction was performed using water instead of a buffer solution (Entry 5). When water was used, it was confirmed by TLC analysis that a larger amount of 12a was produced, but 12b did not disappear. Therefore, methanol was added in the expectation that when the mixing of the organic phase and the aqueous phase was promoted, the acid present in the system would effectively hydrolyze 12b. As a result, the desired diol 12a was successfully obtained in a yield of 90%.

TABLE 3

Table 3. Tolerability of NAPOM Group

| Entry | Substrate | Reagents | Product | Yield/% |
|---|---|---|---|---|
| 1 | PhCH₂CH₂CH₂-OR<br>1b: R = NAPOM<br>13: R = NAP | Protonic/Lewis Acids | 1b<br>1a<br>13 | Trace<br>94<br>96 |
| 2 | 1b: R = NAPOM<br>14: R = PMB | Protonic/Lewis Acids | 1b<br>1a<br>14 | ND, but 1b and 14 will decrease at the similar rate to give 1a. |
| 3 | 1b: R = NAPOM<br>15: R = PMBOM | Protonic/Lewis Acids | 1b<br>1a<br>15 | ND but 1b and 15 will decrease at the similar rate to give 1a. |
| 4 | 1b: R = NAPOM<br>14: R = PMB | CAN (3 eq) | 1b<br>1a<br>14 | Quant.<br>Quant.<br>Trace |
| 5 | 1b: R = NAPOM<br>15: R = PMBOM | CAN (3 eq) | 1b<br>1a<br>15 | ND, but 1b will be selectively recovered. |
| 6 | 1b: R = NAPOM<br>14: R = PMB | H₂, Pd/C | 1b<br>1a<br>14 | Trace<br>Quant.<br>94 |
| 7 | 1b: R = NAPOM<br>15: R = PMBOM | H₂, Pd/C | 1b<br>1a<br>15 | ND, but 15 will be/ selectively recovered. |

A 1:1 (mol/mol) mixture of substrates was used.

Since a mild introduction method and a reliable removal method for the NAPOM group were successfully found, it was decided to finally examine the properties of the NAPOM group as a protecting group. Considering the stability of an acetal against an acid, the NAPOM group can be selectively removed in the presence of a NAP group by allowing an acid to act. In addition, it is considered that the NAPOM group has almost the same level of acid resistance as a PMB group and a PMBOM group. Therefore, Entries 1 to 7 can be objects of experiments as shown in the above table 3.

For example, in detailed experiments on Entry 4, when stability under oxidative conditions was examined, it was shown that the NAPOM group was stable under conditions in which 3 equivalents of CAN was allowed to act in acetone-water, under which conditions the PMB group (Entry 4) was removed (it is considered that the same also applies to the PMBOM group: Entry 5) ("Quant." in the table represents quantitative, and "Trace" represents a very slight amount). Conversely, it is considered that under catalytic reduction conditions in which Pd is used as a catalyst, the NAPOM group undergoes hydrogenolysis more quickly than PMB and PMBOM.

In addition to this, it has been confirmed that also for Entry 1 and Entry 6 in the above Table 3, the desired reactions proceeded according to the following chemical formulas (see Examples described later).

[Formula 10]

Entry 1

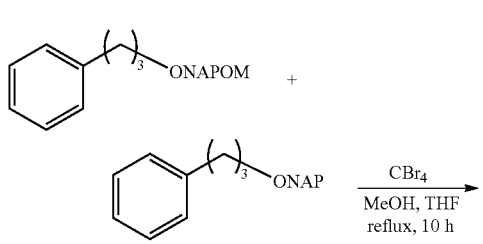

[Formula 11]

Entry 6

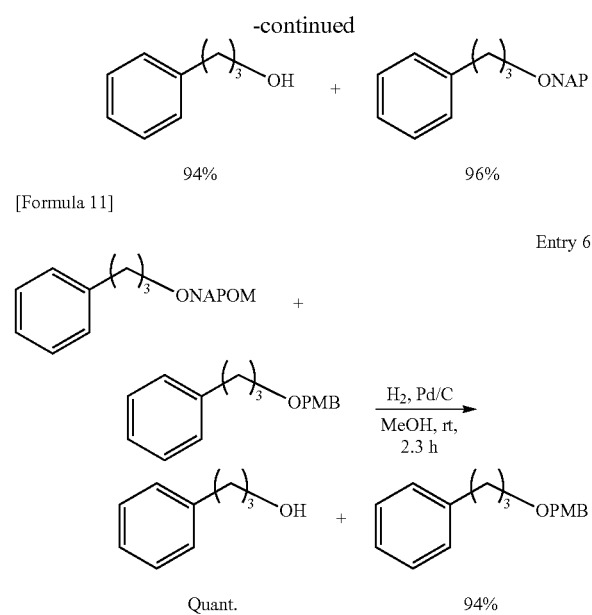

The detailed experimental results of the reactions listed in the above tables and the obtained identification data are shown below.

EXAMPLE 1

NAPOM Ether 1b

Finely ground calcium chloride (220 mg, 1.98 mmol) and ethyldiisopropylamine (1.13 mL, 6.48 mmol) were added to a dichloromethane (19 mL) solution of an alcohol 1a (220 mg, 1.61 mmol), and the mixture was stirred at room temperature for 30 minutes. NAPOM chloride (92%, 667 mg, 2.97 mmol) was added, and the mixture was further stirred at room temperature for 6.5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1) to obtain a NAPOM ether 1b (450 mg, 1.47 mmol, 91%) as a colorless oily material. NAPOM ether 1b:

$^1$H-NMR (400 MHz, CDCl$_3$): δ 7.84-7.80 (m, 4H), 7.52-7.44 (m, 3H), 7.29-7.26 (m, 2H), 7.20-7.17 (m, 3H), 4.82 (s, 2H), 4.78 (s, 2H), 3.65 (t, J=6.4 Hz, 2H), 2.72 (t, J=7.8 Hz, 2H), 1.95 (tt, J=7.8, 6.4 Hz, 2H).

EXAMPLE 2

NAPOM Ether 2b

Finely ground calcium chloride (250 mg, 2.25 mmol) and ethyldiisopropylamine (1.74 mL, 9.99 mmol) were added to a dichloromethane (16 mL) solution of an alcohol 2a (250 mg, 1.66 mmol), and the mixture was stirred at room temperature for 30 minutes. NAPOM chloride (92%, 1.13 g, 5.44 mmol) was added, and the mixture was further stirred at room temperature for 6.5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1) to obtain a NAPOM ether 2b (478 mg, 1.49 mmol, 90%) as a colorless oily material. NAPOM ether 2b:

$^1$H-NMR (400 MHz, CDCl$_3$): δ 7.84-7.80 (m, 4H), 7.52-7.45 (m, 3H), 7.29-7.25 (m, 2H), 7.20-7.16 (m, 3H), 4.90 (d, J=6.9 Hz, 1H), 4.83 (d, J=7.3 Hz, 1H), 4.81 (s, 2H), 3.85 (qdd, J=6.4, 6.0, 6.0, 1H), 2.82-2.75 (m, 1H), 2.71-2.64 (m, 1H), 1.97-1.88 (m, 1H), 1.83-1.74 (m, 1H), 1.26 (d, J=6.4 Hz, 3H).

EXAMPLE 3

NAPOM Ether 3b

Finely ground calcium chloride (196 mg, 1.77 mmol) and ethyldiisopropylamine (1.29 mL, 7.14 mmol) were added to a dichloromethane (3 mL) solution of an alcohol 3a (196 mg, 1.19 mmol), and the mixture was stirred at room temperature for 30 minutes. NAPOM chloride (92%, 799 mg, 3.56 mmol) was added, and the mixture was further stirred at room temperature for 32.5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1) to obtain a NAPOM ether 3b (383 mg, 1.15 mmol, 96%) as a colorless oily material. NAPOM ether 3b:

$^1$H-NMR (400 MHz, CDCl$_3$): δ 7.83-7.80 (m, 4H), 7.49-7.44 (m, 3H), 7.27-7.24 (m, 2H), 7.19-7.15 (m, 3H), 4.94 (s, 2H), 4.83 (s, 2H), 2.74-2.69 (m, 1H), 1.89-1.84 (m, 2H), 1.35 (s, 6H).

EXAMPLE 4

NAPOM Ester 4b

Finely ground calcium chloride (200 mg, 1.80 mmol) and ethyldiisopropylamine (926 µL, 5.32 mmol) were added to a dichloromethane (15 mL) solution of a carboxylic acid 4a (200 mg, 1.33 mmol), and the mixture was stirred at room temperature for 30 minutes. NAPOM chloride (92%, 596 mg, 2.66 mmol) was added, and the mixture was further stirred at room temperature for 10.5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→20/1) to obtain a NAPOM ester 4b (402 mg, 1.25 mmol, 94%) as a pale yellow oily material. NAPOM ester 4b: $^1$H-NMR (400 MHz, CDCl$_3$): δ 7.84-7.77 (m, 4H), 7.52-7.41 (m, 3H), 7.30-7.26 (m, 2H), 7.22-7.16 (m, 3H), 5.40 (s, 2H), 4.78 (s, 2H), 2.93 (t, J=7.8 Hz, 2H), 2.64 (t, J=7.8 Hz, 2H).

EXAMPLE 5

NAPOM Ether 5b

Finely ground calcium chloride (200 mg, 1.80 mmol) and ethyldiisopropylamine (1.02 mL, 5.88 mmol) were added to a dichloromethane (15 mL) solution of a phenol 5a (200 mg, 1.46 mmol), and the mixture was stirred at room temperature for 30 minutes. NAPOM chloride (92%, 670 mg, 2.99 mmol) was added, and the mixture was further stirred at room temperature for 5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by recrystallization using a hexane/ethyl acetate=3/1 solvent, to obtain a NAPOM ether 5b (407 mg, 1.33 mmol, 91%) as colorless needle crystals. NAPOM ether 5b: $^1$H-NMR (400 MHz, CDCl$_3$): δ 7.96-7.93 (m, 2H), 7.84-7.80 (m, 3H), 7.78 (s, 1H), 7.52-7.46 (m, 2H), 7.42 (dd, J=8.5, 1.6 Hz, 1H), 7.16-7.13 (m, 2H), 5.39 (s, 2H), 4.88 (s, 2H), 2.57 (s, 3H).

EXAMPLE 6

NAPOM Sulfide 6b

Finely ground calcium chloride (214 mg, 1.93 mmol) and ethyldiisopropylamine (1.33 mL, 7.74 mmol) were added to a dichloromethane (16.5 mL) solution of a thiol 6a (214 mg, 1.55 mmol), and the mixture was stirred at room temperature for 30 minutes. NAPOM chloride (92%, 868 mg, 3.88 mmol) was added, and the mixture was further stirred at room temperature for 13 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1) to obtain a NAPOM sulfide 6b (419 mg, 1.36 mmol, 88%) as a colorless oily material. NAPOM sulfide 6b: $^1$H-NMR (400 MHz, CDCl$_3$): δ 7.85-7.81 (m, 3H), 7.79 (s, 1H), 7.52-7.44 (m, 3H), 7.31-7.27 (m, 2H), 7.23-7.20 (m, 3H), 4.78 (s, 2H), 4.77 (s, 2H), 3.00-2.91 (m, 4H).

EXAMPLE 7

Deprotection of NAPOM Ether 1b

The NAPOM ether 1b (153 mg, 0.50 mmol) was dissolved in a dichloromethane-pH 7.0 phosphate buffer solution 18:1 mixed solvent (5 mL), and 2,3-dichloro-5,6-dicyano-p-benzoquinone (DDQ, 170 mg, 0.75 mmol) was added at 0° C. The mixture was vigorously stirred at room temperature for 2 hours and then diluted with ether at 0° C., and a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1→2/1) to obtain the alcohol 1a (66.9 mg, 0.491 mmol, 98%) as a pale yellow oily material. Alcohol 1a: $^1$H-NMR (400 MHz, CDCl$_3$): δ 7.31-7.27 (m, 2H), 7.21-7.17 (m, 3H), 3.68 (t, J=6.0 Hz, 2H), 2.71 (t, J=7.8 Hz, 2H), 1.94-1.87 (m, 2H), 1.29 (brs, 1H). (This chart agrees with the chart of a commercial product.)

EXAMPLE 8

Deprotection of NAPOM Ether 2b

The NAPOM ether 2b (160 mg, 0.50 mmol) was dissolved in a dichloromethane-pH 7.0 phosphate buffer solution 18:1 mixed solvent (5 mL), and 2,3-dichloro-5,6-dicyano-p-benzoquinone (DDQ, 170 mg, 0.75 mmol) was added at 0° C. The mixture was vigorously stirred at room temperature for 3.5 hours and then diluted with ether at 0° C., and a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1→2/1) to obtain the alcohol 2a (71.7 mg, 0.477 mmol, 96%) as a pale yellow oily material. Alcohol 2a: $^1$H-NMR (400 MHz, CDCl$_3$): δ 7.30-7.27 (m, 2H), 7.21-7.17 (m, 3H), 3.83 (qdd, J=6.4, 6.0, 6.0 Hz, 1H), 2.80-2.73 (m, 1H), 2.71-2.64 (m, 1H), 1.81-1.74 (m, 2H), 1.35 (brs, 1H), 1.23 (d, J=6.0 Hz, 3H). (This chart agrees with the chart of a commercial product.)

EXAMPLE 9

Deprotection of NAPOM Ether 3b

The NAPOM ether 3b (167 mg, 0.50 mmol) was dissolved in a dichloromethane-pH 7.0 phosphate buffer solution 18:1 mixed solvent (5 mL), 2,3-dichloro-5,6-dicyano-p-benzoquinone (DDQ, 170 mg, 0.75 mmol) was added at 0° C., and the mixture was vigorously stirred at room temperature for 2 hours. The mixture was diluted with ether at 0° C., and then a saturated sodium hydrogen carbonate aqueous solution and a saturated sodium thiosulfate aqueous solution were added to stop the reaction.

The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1) to obtain the alcohol 3a (74.5 mg, 0.454 mmol, 91%) as a pale yellow oily material. Alcohol 3a: $^1$H-NMR (400 MHz, CDCl$_3$): δ 7.30-7.27 (m, 2H), 7.21-7.16 (m, 3H), 2.72-2.68 (m, 2H), 1.82-1.77 (m, 2H), 1.29 (s, 6H). (This chart agrees with the chart of a commercial product.)

EXAMPLE 10

Deprotection of NAPOM Ether 5b

The NAPOM ether 5b (153 mg, 0.50 mmol) was dissolved in a dichloromethane-pH 7.0 phosphate buffer solution 18:1 mixed solvent (5 mL), 2,3-dichloro-5,6-dicyano-p-benzoquinone (DDQ, 227 mg, 1.00 mmol) was added at 0° C., and the mixture was vigorously stirred at room temperature for 22.5 hours. The mixture was cooled to 0° C. and diluted with ether, and then a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=5/1→2/1) to obtain the phenol 5a (71.3 mg, 0.524 mmol, quantitative) as a pale yellow oily material. Phenol 5a: $^1$H-NMR (400 MHz, CDCl$_3$): δ 7.92-7.89 (m, 2H), 6.91-6.88 (m, 2H), 6.40 (brs, 1H), 2.57 (s, 3H). (This chart agrees with the chart of a commercial product.)

EXAMPLE 11

Deprotection of NAPOM Sulfide 6b

The NAPOM sulfide 6b (154 mg, 0.50 mmol) was dissolved in a dichloromethane-pH 7.0 phosphate buffer solution 18:1 mixed solvent (5 mL), and 2,3-dichloro-5,6-dicyano-p-benzoquinone (DDQ, 293 mg, 1.29 mmol) was added at 0° C. The mixture was vigorously stirred at room temperature for 29.5 hours and then diluted with ether at 0° C., and a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=100/1) to obtain a disulfide 6c (64.4 mg, 0.235 mmol, 94%) as a colorless oily material. Disulfide 6c: $^1$H-NMR (400 MHz, CDCl$_3$): δ 7.32-7.28 (m, 4H), 7.24-7.19 (m, 6H), 3.02-2.98 (m, 4H), 2.96-2.92 (m, 4H); $^{13}$C-NMR (100 MHz, CDCl$_3$): δ 140.1, 128.7 (two overlapped signals), 128.6 (two overlapped signals), 126.5, 40.3, 35.8. (The values agree with literature values. Banfield, S. C.; Omori, A. T.; Leisch, H.; Hudlicky, T. J. Org. Chem. 2007, 72, 4989-4992.)

EXAMPLE 12

NAPOM Ether 8a (Table 2, Entry 1)

Finely ground calcium chloride (270 mg, 2.43 mmol) was added to a dichloromethane (15 mL) solution of 2-hydroxy-1-phenylethyl acetate 7 (270 mg, 1.50 mmol), and the mixture was stirred for 30 minutes. The mixture was cooled to 0° C., ethyldiisopropylamine (1.55 mL, 9.00 mmol) and NAPOM chloride (92%, 1.01 g, 4.50 mmol) were added, and the mixture was stirred at room temperature for 50 hours. The mixture was cooled to 0° C. and diluted with ether, and then a saturated potassium hydrogen sulfate aqueous solution was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=30/1→10/1→7/1) to obtain a NAPOM ether 8a (248 mg, 0.71 mmol, 47%) as a colorless oily material and an acyl migration product 8b (101 mg, 0.289 mmol, 19%) as a colorless oily material. NAPOM ether 8a: $^1$H-NMR (400 MHz, CDCl$_3$): δ 7.83-7.81 (m, 3H), 7.75 (s, 1H), 7.52-7.45 (m, 2H), 7.42 (dd, J=8.2, 1.4 Hz, 1H), 7.36-7.29 (m, 5H), 5.98 (dd, J=7.8, 4.1 Hz, 1H), 4.81 (d, J=12.6 Hz, 1H), 4.79 (d, J=12.6 Hz, 1H), 4.69 (d, J=12.6 Hz, 1H), 4.66 (d, J=12.6 Hz, 1H), 3.93 (dd, J=11.0, 7.8 Hz, 1H), 3.83 (dd, J=11.0, 4.1 Hz, 1H), 2.12 (s, 3H). NAPOM ether 8b: $^1$H-NMR (400 MHz, CDCl$_3$): δ 7.84-7.80 (m, 3H), 7.72 (s, 1H), 7.50-7.44 (m, 3H), 7.41-7.31 (m, 5H), 5.00 (dd, J=8.0, 4.1 Hz, 1H), 4.89 (d, J=11.7 Hz, 1H), 4.84 (d, J=6.9 Hz, 1H), 4.74 (d, J=6.9 Hz, 1H), 4.68 (d, J=11.7 Hz, 1H), 4.31 (dd, J=11.7, 8.0 Hz, 1H), 4.25 (dd, J=11.7, 4.1 Hz, 1H), 2.05 (s, 3H).

EXAMPLE 13

NAPOM Ether 8a (Table 2, Entry 2)

Finely ground calcium chloride (270 mg, 2.43 mmol) was added to a dichloromethane (15 mL) solution of the 2-hydroxy-1-phenylethyl acetate 7 (270 mg, 1.50 mmol), and the mixture was stirred for 30 minutes. The mixture was cooled to 0° C., 2,6-lutidine (1.39 mL, 18.0 mmol), tetrabutylammonium iodide (TBAI, 277 mg, 0.75 mmol), and NAPOM chloride (92%, 2.01 g, 9.00 mmol) were added, and the mixture was further stirred at room temperature for 12 hours. The mixture was cooled to 0° C. and diluted with ether, and then a saturated potassium hydrogen sulfate aqueous solution was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=30/1→10/1→7/1) to obtain the NAPOM ether 8a (466 mg, 1.33 mmol, 89%) as a colorless oily material and an acyl migration product 8b (13.2 mg, 0.0377 mmol, 3%) as a colorless oily material.

EXAMPLE 14

NAPOM Ether 10a

Finely ground calcium chloride (235 mg, 2.12 mmol) and 2,6-lutidine (1.39 mL, 18.0 mmol) were added to a dichloromethane (15 mL) solution of benzyl alcohol 9 (235 mg, 1.50 mmol), and the mixture was stirred for 30 minutes. The mixture was cooled to 0° C., NAPOM chloride (92%, 2.02 g, 9.00 mmol) was added, and the mixture was further stirred at room temperature for 16 hours. The mixture was cooled to 0° C. and diluted with ether, and then a saturated potassium hydrogen sulfate aqueous solution was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1→20/1) to obtain a NAPOM ether 10a (369 mg, 1.13 mmol, 75%) as a colorless powdery solid. NAPOM ether 10a: $^1$H-NMR (400 MHz, CDCl$_3$): δ 7.85-7.80 (m, 4H), 7.51-7.45 (m, 3H), 7.39-7.34 (m, 4H), 4.89 (s, 2H), 4.81 (s, 2H), 4.69 (s, 2H), 4.59 (s, 2H).

EXAMPLE 15

Mono-NAPOM Ether 11

A methanol (5.6 mL) solution of the NAPOM ether 8a (298 mg, 0.850 mmol) was cooled to 0° C., sodium methoxide (91.8 mg, 1.70 mmol) was added, and then the mixture was stirred at room temperature for 2.5 hours. The mixture was cooled to 0° C. and diluted with ether, and then water was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a mono-NAPOM ether 11 (257.9 mg, 0.84 mmol) as a colorless powdery solid. Mono-NAPOM ether 11: $^1$H-NMR (400 MHz, CDCl$_3$): δ 7.85-7.83 (m, 3H), 7.51-7.44 (m, 3H), 7.79 (s, 1H), 7.39-7.27 (m, 5H), 4.92-4.86 (m, 3H), 4.79 (d, J=12.1 Hz, 1H), 4.76 (d, J=12.1 Hz, 1H), 3.85 (dd, J=10.5, 3.2 Hz, 1H), 3.67 (dd, J=10.5, 8.7 Hz, 1H), 2.97 (d, J=2.3 Hz, 1H).

EXAMPLE 16

Deprotection of Mono-NAPOM Ether 11 (Table 2, Entry 4)

The mono-NAPOM ether 11 (185 mg, 0.60 mmol) was dissolved in a dichloromethane-pH 7.0 phosphate buffer solution 18:1 mixed solvent (6 mL), 2,3-dichloro-5,6-dicyano-p-benzoquinone (DDQ, 204 mg, 0.90 mmol) was added at 0° C., and the mixture was vigorously stirred at room temperature for 3 hours. The mixture was cooled to 0° C. and diluted with ether, and then a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=50/1→30/1→5/1→2/1→1/1) to obtain a diol 12a (22.3 mg, 0.161 mmol, 27%) as a colorless powdery solid and a cyclic acetal 12b (94.4 mg, 0.308 mmol, 51%) as a pale yellow oily material. Diol 12a: $^1$H-NMR (400 MHz, CDCl$_3$): δ 7.37-7.28 (m, 5H), 4.83 (dd, J=8.2, 3.7 Hz, 1H), 3.77 (dd, J=11.5, 3.7 Hz, 1H), 3.67 (dd, J=11.5, 8.2 Hz, 1H), 2.71 (brs, 1H), 2.27 (brs, 1H). Cyclic acetal 12b: $^1$H-NMR (400 MHz, CDCl$_3$): δ 8.03-7.78 (m, 8H), 7.72-7.45 (m, 6H), 7.42-7.26 (m, 10H), 6.29 (s, 1H), 6.01 (s, 1H), 5.36 (d, J=7.3 Hz, 1H), 5.28 (d, J=7.3 Hz, 1H), 5.19 (d, J=6.4 Hz, 1H), 5.14-5.12 (m, 2H), 5.04 (dd, J=9.2, 1.4 Hz, 1H), 4.10 (dd, J=12.4, 1.8 Hz, 1H), 4.01 (dd, J=12.4, 1.8 Hz, 1H), 3.79 (dd, J=12.4, 9.2 Hz, 1H), 3.71 (dd, J=12.4, 9.2 Hz, 1H).

EXAMPLE 17

Deprotection of Mono-NAPOM Ether 11 (Table 2, Entry 5)

The mono-NAPOM ether 11 (30.4 mg, 0.0986 mmol) was dissolved in a dichloromethane-water 2:1 mixed solvent (1.5 mL), 2,3-dichloro-5,6-dicyano-p-benzoquinone (DDQ, 35 mg, 0.15 mmol) was added at 0° C., and the mixture was vigorously stirred at room temperature for 2.5 hours. Then, methanol (0.5 mL) was added, and the mixture was further stirred for 4 hours. The mixture was cooled to 0° C. and diluted with ethyl acetate, and then a saturated sodium hydrogen carbonate aqueous solution and a saturated sodium thiosulfate aqueous solution were added to stop the reaction. The obtained mixture was subjected to extraction with ethyl acetate three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=4/1→2/1→1/1) to obtain the diol 12a (12.2 mg, 0.0883 mmol, 90%) as a colorless powdery solid.

EXAMPLE 18

Selective Removal of PMB Group

The NAPOM ether 1b (153 mg, 0.50 mmol) and a PMB ether 14 (135 mg, 0.50 mmol) were dissolved in an acetone-water 9:1 mixed solvent (5 mL), cerium ammonium nitrate (CAN, 822 mg, 1.50 mmol) was added at 0° C., and the mixture was stirred at room temperature for 6 hours. The mixture was cooled to 0° C. and diluted with ether, and then a saturated sodium hydrogen carbonate aqueous solution and a saturated sodium thiosulfate aqueous solution were added to stop the reaction.

The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=20/1→10/1→3/1) to obtain the alcohol 1a (76.9 mg, 0.565 mmol, quantitative) as a pale yellow oily material. At the same time, the unreacted NAPOM ether 1b (165 mg, 0.538 mmol, quantitative) was recovered.

EXAMPLE 19

1-NAPOM Ether 1c

Ethyldiisopropylamine (1.03 mL, 6.00 mmol) and 1-NAPOM chloride (89%, 695 mg, 3.00 mmol) were added to a dichloromethane (15 mL) solution of the alcohol 1a (204 mg, 1.50 mmol) at room temperature, and the mixture was further stirred at room temperature for 7.4 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→40/1) to obtain a 1-NAPOM ether 1c (469 mg, 1.53 mmol, quantitative) as a colorless oily material. 1-NAPOM ether 1c: $^1$H-NMR (400 MHz, CDCl$_3$): d 8.10 (d, J=7.8 Hz, 1H), 7.88-7.81 (m, 2H), 7.55-7.42 (m, 4H), 7.30-7.26 (m, 2H), 7.21-7.17 (m, 3H), 5.08 (s, 2H), 4.83 (s, 2H), 3.64 (t, J=6.4 Hz, 2H), 2.72 (t=7.8 Hz, 2H), 1.95 (tt, J=6.4, 6.4 Hz, 2H).

EXAMPLE 20

1-NAPOM Ether 2c

Ethyldiisopropylamine (1.03 mL, 6.00 mmol) and 1-NAPOM chloride (87%, 713 mg, 3.00 mmol) were added to a dichloromethane (15 mL) solution of the alcohol 2a (225 mg, 1.50 mmol) at room temperature, and the mixture was further stirred at room temperature for 16 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→20/1) to obtain a 1-NAPOM ether 2c (430 mg, 1.34 mmol, 90%) as a colorless oily material. 1-NAPOM ether 2c: $^1$H-NMR (400 MHz, CDCl$_3$): d 8.10 (d, J=7.8 Hz, 1H), 7.88-7.86 (m, 1H), 7.82 (d, J=8.2 Hz, 1H), 7.55-7.42 (m, 4H), 7.30-0.25 (m, 2H), 7.22-7.16 (m, 3H), 5.10 (s, 2H), 4.91 (d, J=7.3 Hz, 1H), 4.85 (d, J=6.9 Hz, 1H), 3.85 (qdd, J=6.2, 6.2, 6.2 Hz, 1H), 2.82-2.75 (m, 1H), 2.72-2.64 (m, 1H), 1.97-1.88 (m, 1H), 1.84-1.75 (m, 1H), 1.26 (d, J=6.0 Hz, 3H).

EXAMPLE 21

1-NAPOM Ether 3c

Ethyldiisopropylamine (1.55 mL, 9.00 mmol) and 1-NAPOM chloride (89%, 1.04 g, 4.50 mmol) were added to a dichloromethane (3 mL) solution of the alcohol 3a (246 mg, 1.50 mmol) at room temperature, and the mixture was further stirred at room temperature for 19 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1) to obtain a 1-NAPOM ether 3c (480 mg, 1.44 mmol, 96%) as a colorless oily material. 1-NAPOM ether 3c: $^1$H-NMR (400 MHz, CDCl$_3$): d 8.11 (d, J=8.2 Hz, 1H), 7.87 (d, J=7.8 Hz, 1H), 7.81 (d, J=8.2 Hz, 1H), 7.54-7.41 (m, 4H), 7.25-7.23 (m, 2H), 7.20-7.15 (m, 3H), 5.12 (s, 2H), 4.95 (s, 2H), 2.74-2.70 (m, 2H), 1.89-1.84 (m, 2H), 1.34 (s, 6H).

EXAMPLE 22

Deprotection of 1-NAPOM Ether 1c

The 1-NAPOM ether 1c (30.6 mg, 0.100 mmol) was dissolved in a dichloromethane-H$_2$O 4:1 mixed solvent (1 mL), and 2,3-dichloro-5,6-dicyano-p-benzoquinone (DDQ, 68.1 mg, 0.300 mmol) was added at 0° C. The mixture was vigorously stirred under reflux conditions (45° C.) for 19.5 hours and then diluted with ether at 0° C., and a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1→2/1) to obtain the alcohol 1a (8.7 mg, 0.0639 mmol, 64%) as a pale yellow oily material. Alcohol 1a: $^1$H-NMR (400 MHz, CDCl$_3$): d 7.31-7.27 (m, 2H), 7.21-7.17 (m, 3H), 3.68 (t, J=6.0 Hz, 2H), 2.71 (t, J=7.8 Hz, 2H), 1.94-1.87 (m, 2H), 1.29 (brs, 1H). (This chart agrees with the chart of a commercial product.)

EXAMPLE 23

Deprotection of 1-NAPOM Ether 2c

The 1-NAPOM ether 2c (160 mg, 0.50 mmol) was dissolved in a dichloromethane-H$_2$O 4:1 mixed solvent (1 mL), and 2,3-dichloro-5,6-dicyano-p-benzoquinone (DDQ, 170 mg, 0.75 mmol) was added at 0° C. The mixture was vigorously stirred under reflux conditions (45° C.) for 15 hours and then diluted with ether at 0° C., and a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1→3/1) to obtain the alcohol 2a (12.9 mg, 0.0859 mmol, 86%) as a pale yellow oily material. Alcohol 2a: $^1$H-NMR (400 MHz, CDCl$_3$): d 7.30-7.27 (m, 2H), 7.21-7.17 (m, 3H), 3.83 (qdd, J=6.4, 6.0, 6.0 Hz, 1H), 2.80-2.73 (m, 1H), 2.71-2.64 (m, 1H), 1.81-1.74 (m, 2H), 1.35 (brs, 1H), 1.23 (d, J=6.0 Hz, 3H). (This chart agrees with the chart of a commercial product.)

EXAMPLE 24

Deprotection of 1-NAPOM Ether 3c

The 1-NAPOM ether 3c (33.4 mg, 0.100 mmol) was dissolved in a dichloromethane-H$_2$O 4:1 mixed solvent (1 mL), 2,3-dichloro-5,6-dicyano-p-benzoquinone (DDQ, 68.1 mg, 0.300 mmol) was added at 0° C., and the mixture was vigorously stirred at room temperature for 27 hours. The mixture was diluted with ether at 0° C., and then a saturated sodium hydrogen carbonate aqueous solution and a saturated sodium thiosulfate aqueous solution were added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (pentane/ether=10/1→5/1→3/1) to obtain the alcohol 3a (16.2 mg, 0.0986 mmol, 99%) as a pale yellow oily material. Alcohol 3a: $^1$H-NMR (400 MHz, CDCl$_3$): d 7.30-7.27 (m, 2H), 7.21-7.16 (m, 3H), 2.72-2.68 (m, 2H), 1.82-1.77 (m, 2H), 1.29 (s, 6H). (This chart agrees with the chart of a commercial product.)

EXAMPLE 25

NAPOM Group Introduction Using 2,6-Di t-butyl-4-methylpyridine (DTBMP)

Finely ground calcium chloride (18.0 mg, 0.16 mmol) was added to a dichloromethane (1 mL) solution of the 2-hydroxy-1-phenylethyl acetate 7 (18.0 mg, 0.100 mmol). The mixture was cooled to 0° C., 2,6-di-tert-butyl-4-methylpyridine (DTBMP, 246.4 mg, 1.20 mmol), tetrabutylammonium iodide (TBAI, 18.5 mg, 0.0500 mmol), and NAPOM chloride (94%, 132 mg, 0.600 mmol) were added, and the mixture was stirred at room temperature for 5 hours. The mixture was cooled to 0° C. and diluted with ether, and then a saturated potassium hydrogen sulfate aqueous solution was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=30/1→10/1→5/1) to obtain the NAPOM ether 8a (34.5 mg, 0.0985 mmol, 99%) as a colorless oily material.

[Formula 12]

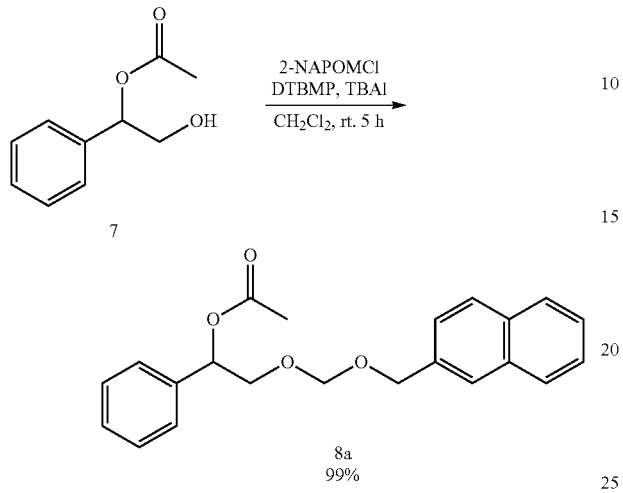

EXAMPLE 26

Introduction of NAPOM Group Using Proton Sponge

Finely ground calcium chloride (180 mg, 1.62 mmol) was added to a toluene (3.5 mL) solution of 2-hydroxy-2-phenylethyl acetate 16 (180 mg, 1.00 mmol). The mixture was cooled to 0° C., 1,8-bis(dimethylamino)naphthalene (proton sponge, 2.57 g, 12.0 mmol), tetrabutylammonium iodide (TBAI, 185 mg, 0.50 mmol), and NAPOM chloride (94%, 1.32 g, 6.00 mmol) were added, and the mixture was stirred at room temperature for 30 hours. The mixture was cooled to 0° C. and diluted with ether, and then a saturated potassium hydrogen sulfate aqueous solution was added to stop the reaction. The obtained mixture was subjected to extraction with ether three times, and the organic phases were combined, washed with a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=30/1→10/1→5/1) to obtain a NAPOM ether 8b (298 mg, 0.849 mmol, 85%) as a colorless oily material and an acyl migration product 8a (56.1 mg, 0.160 mmol, 16%) as a colorless oily material.

[Formula 13]

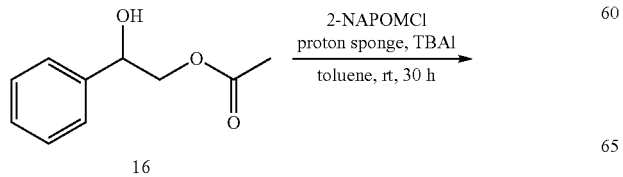

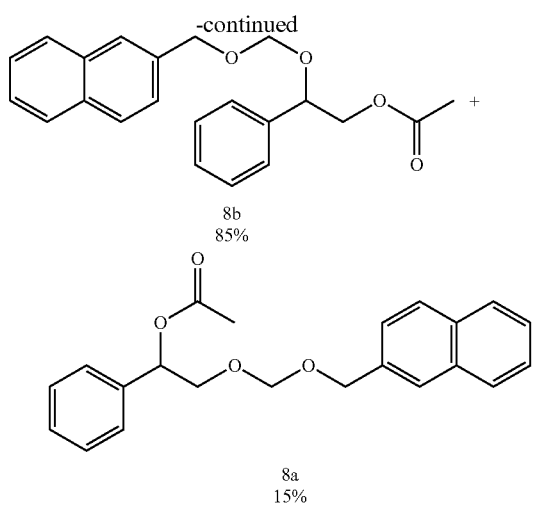

EXAMPLE 27

Method for Producing 2-NAPOMBr

Paraformaldehyde (5.39 g, 0.152 mol) was added to a mixed solution of 2-naphthalenemethanol 17 (24.0 g, 0.152 mol) in pentane (250 mL) and dichloromethane (50 mL), and the mixture was cooled to −20° C. Hydrobromic acid (48% aqueous solution, 140 mL, 1.23 mol) was slowly added to anhydrous magnesium sulfate (300 g) weighed into another flask, using a dropping funnel, to generate hydrogen bromide gas. While the generated hydrogen bromide gas was blown into the reaction solution through a glass tube, the reaction solution was stirred at −20° C. for 5 hours. Then, argon gas was blown for 1 hour, and the reaction solution was filtered under an argon atmosphere. The filtrate was concentrated and dried to obtain 2-NAPOM bromide 18 (12.1 g, 0.0481 mol, 32%) as a white solid. 2-NAPOM bromide 18: 1H-NMR (400 MHz, CDlC3): δ7.88-7.80 (m, 4H), 7.53-7.45 (m, 3H), 5.75 (s, 2H), 4.89 (s, 2H).

[Formula 14]

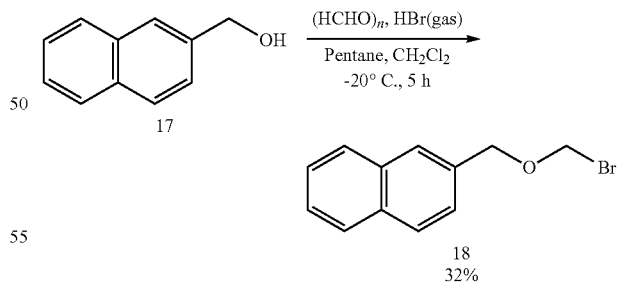

EXAMPLE 28

2-NAPOM Protection of Alcohol Using 2-NAPOMBr

Ethyldiisopropylamine (0.513 mL, 3.00 mmol) and 2-NAPOM bromide (377 mg, 1.50 mmol) were added to a toluene (1 mL) solution of the alcohol 3a (82.1 mg, 0.500 mmol), and the mixture was stirred at room temperature for 15.5 hours. The mixture was cooled to 0° C. and diluted with ether, and then water was added to stop the reaction. The obtained mixture was subjected to extraction with ether three times, and the organic phases were combined, washed with a saturated potassium hydrogen sulfate aqueous solution and a saturated sodium chloride aqueous solution, and then dried over anhydrous sodium sulfate. The desiccant was filtered off, and then the filtrate was concentrated to obtain a crude product. The crude product was purified by silica gel column chromatography (hexane/ethyl acetate=50/1→30/1) to obtain the NAPOM ether 3b (125 mg, 0.374 mmol, 75%) as a colorless oily material and the raw material 3a (8.6 mg, 0.0524 mmol, 10%) as a colorless oily material.

[Formula 15]

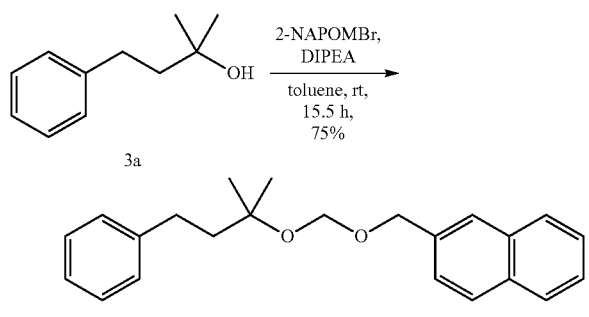

EXAMPLE 29

Deprotection of NAPOM Ether 1b (Table 3, Entry 1)

CBr$_4$ (6.0 mg, 0.018 mmol), 2-naphthylmethyl 3-phenyl-propyl ether (27.6 mg, 0.100 mmol), and 2-naphthyl-methoxymethyl 3-phenylpropyl ether (30.6 mg, 0.100 mmol) were added to a mixed solution of a methanol (MeOH) solution (500 µL) and a THF solution (50 µL) at 0° C. The mixture was stirred under reflux conditions for 10 hours, and then the reaction liquid was diluted with ether, and a saturated sodium hydrogen carbonate aqueous solution was added at 0° C. to stop the reaction. The obtained mixture was subjected to extraction with ether, and the organic phases were combined, washed with a saturated sodium chloride aqueous solution, and then dried over anhydrous sodium sulfate. The desiccant was filtered off, and the filtrate was concentrated under reduced pressure to obtain a crude product. The crude product was purified by silica gel column chromatography (pentane/ether=50/1→30/1→10/1→5/1→1/1) to obtain a NAP ether (26.6 mg, 0.0962 mmol, 96%) and 3-phenyl-1-propanol (12.8 mg, 0.0940 mmol, 94%).

EXAMPLE 30

Selective Deprotection of PMB Ether 15 (Table 3, Entry 4)

2-naphthylmethoxymethyl 3-phenylpropyl ether (153 mg, 0.500 mmol) and p-methoxybenzyl 3-phenylpropyl ether (135 mg, 0.500 mmol) were dissolved in an acetone (4.5 mL)-water (0.5 mL) mixed solvent, and cerium ammonium nitrate (CAN, 548 mg, 1.00 mmol) was added at 0° C. The mixed liquid was vigorously stirred at 0° C. to room temperature for 1 hour, and then CAN (137 mg, 0.25 mmol) was further added at 0° C. The mixed liquid was further vigorously stirred at 0° C. to room temperature for 1.5 hours, and then the reaction liquid was diluted with ether, and a saturated sodium hydrogen carbonate aqueous solution and a saturated sodium thiosulfate aqueous solution were added to stop the reaction. The obtained mixture was subjected to extraction with ether, and the organic phases were combined, washed with a saturated sodium chloride aqueous solution, and then dried over anhydrous sodium sulfate. The desiccant was filtered off, and the filtrate was concentrated under reduced pressure to obtain a crude product. The crude product was purified by silica gel column chromatography (pentane/ether=20/1→10/1→3/1) to obtain a NAPOM ether (165 mg, quantitative) and 3-phenyl-1-propanol (76.9 mg, quantitative).

EXAMPLE 31

Selective Removal of NAPOM Group (Table 3, Entry 6)

A methanol (10 mL) solution of a NAPOM (2-naphthyl-methoxymethyl 3-phenylpropyl) ether (153 mg, 0.500 mmol) and a PMB (p-methoxybenzyl 3-phenylpropyl) ether (135 mg, 0.500 mmol) was added to 10% Pd/C (26.6 mg), and the mixed liquid was vigorously stirred under a hydrogen atmosphere (balloon) at room temperature for 2.25 hours. The reaction liquid was filtered through a celite pad followed by concentration under reduced pressure. The crude product obtained by concentrating the filtrate was purified by silica gel column chromatography (pentane/ether=50/1→30/1→3/1→1/1) to obtain a PMB ether (127 mg, 0.470 mmol, 94%) and 3-phenyl-1-propanol (80.6 mg, quantitative).

In the above Examples, as novel agents for introducing protecting groups for hydroxy groups and/or mercapto groups, novel BOM-based protecting groups, NAPOM derivatives, have been mainly shown. Examples of advantages of the NAPOM group include i) the fact that NAPOMX can be stored, ii) the fact that a side reaction, acyl migration, can be suppressed by using a particular base (for example, 2,6-lutidine or DTBMP) during introduction, iii) the fact that other Bn- and BOM-based protecting groups can be separately removed, and iv) the fact that special consideration for moisture and air is not needed. These advantages are excellent in that not only is a new route proposed for multistep synthesis, but anyone can easily perform protection and deprotection. In addition, according to the above Examples, the NAPOM derivatives are also excellent in that a BOM-based protecting group introduction reaction, which is conventionally performed only in the solvent CH$_2$Cl$_2$, can also be performed in various solvents.

The invention claimed is:
1. An agent for introducing a protecting group for a hydroxy group and/or a mercapto group of a substrate compound having the hydroxy group and/or mercapto group, being represented by the following formula (I):

[Formula 1]

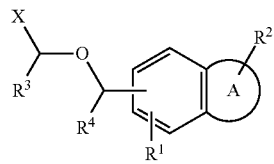

(I)

wherein A is a benzene ring, a pyridine ring, a thiophene ring, a pyrrole ring, a naphthalene ring, or an anthracene ring; each of $R^1$, $R^2$, $R^3$, and $R^4$ is independently a hydrogen atom or a linear or branched alkyl group having 1 to 5 carbon atoms; and X is a halogen atom or $OSO_2R^5$, wherein $R^5$ is an alkyl group, a phenyl group, or a tolyl group.

2. The agent for introducing a protecting group for a hydroxy group and/or a mercapto group according to claim 1,
wherein the agent is represented by any of the following formulas (I)-1 to (I)-6:

[Formula 2]

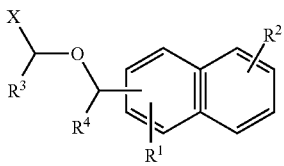

(I)-1

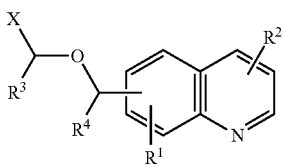

(I)-2

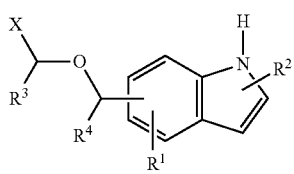

(I)-3

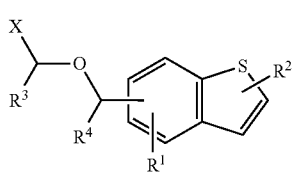

(I)-4

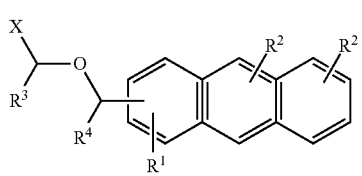

(I)-5

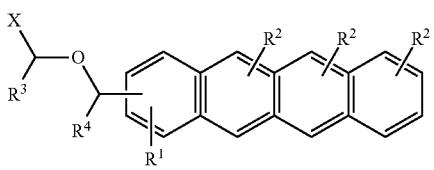

(I)-6 wherein each of $R^1$, one or more $R^2$, $R^3$, and $R^4$ is independently a hydrogen atom or a linear or branched alkyl group having 1 to 5 carbon atoms; and X is a halogen atom or $OSO_2R^5$, wherein $R^5$ is an alkyl group, a phenyl group, or a tolyl group.

3. The agent for introducing a protecting group for a hydroxy group and/or a mercapto group according to claim 1, wherein
the hydroxy group and/or mercapto group contained in the substrate compound are protected by reacting the substrate compound with a compound represented by the formula (I) in coexistence of a base in a reaction.

4. The agent for introducing a protecting group for a hydroxy group and/or a mercapto group according to claim 3, wherein
the reaction is performed by adding a base represented by the following formula (II)-1 or formula (II)-2:

[Formula 3]

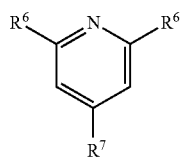

(II)-1

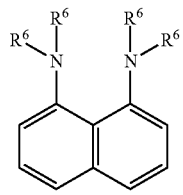

(II)-2 wherein each of $R^6$ and $R^7$ is independently a hydrogen atom or a linear or branched alkyl group having 1 to 5 carbon atoms.

5. The agent for introducing a protecting group for a hydroxy group and/or a mercapto group according to claim 1,
being represented by the following formula (I)-a:

[Formula 4]

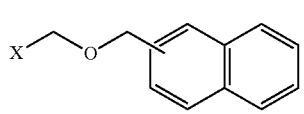

(I)-a wherein X is a halogen atom or $OSO_2R^5$, wherein $R^5$ is an alkyl group, a phenyl group, or a tolyl group.

6. The agent for introducing a protecting group for a hydroxy group and/or a mercapto group according to claim 5, wherein the agent is represented by any of the following formulas (I)-a-1 to (I)-a-4:

[Formula 5]

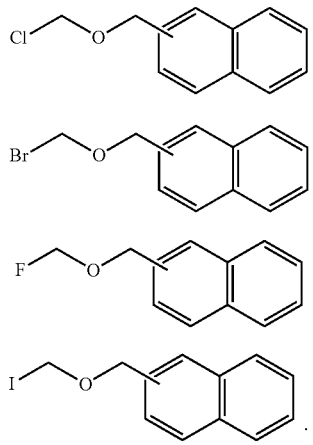

(I)-a-1

(I)-a-2

(I)-a-3

(I)-a-4

7. The agent for introducing a protecting group for a hydroxy group and/or a mercapto group according to claim 1, wherein X is a halogen atom.

8. The agent for introducing a protecting group for a hydroxy group and/or a mercapto group according to claim 1, wherein X is $OSO_2R^5$, wherein $R^5$ is an alkyl group, a phenyl group, or a tolyl group.

9. The agent for introducing a protecting group for a hydroxy group and/or a mercapto group according to claim 2, wherein X is a halogen atom.

10. The agent for introducing a protecting group for a hydroxy group and/or a mercapto group according to claim 2, wherein X is $OSO_2R^5$, wherein $R^5$ is an alkyl group, a phenyl group, or a tolyl group.

11. The agent for introducing a protecting group for a hydroxy group and/or a mercapto group according to claim 5, wherein X is a halogen atom.

12. The agent for introducing a protecting group for a hydroxy group and/or a mercapto group according to claim 5, wherein X is $OSO_2R^5$, wherein $R^5$ is an alkyl group, a phenyl group, or a tolyl group.

13. The agent for introducing a protecting group for a hydroxy group and/or a mercapto group according to claim 1, wherein the reaction is performed in the presence of a solvent, wherein the solvent is toluene.

14. A method for introducing a protecting group for a hydroxy group and/or a mercapto group of a substrate compound, the method comprising reacting the substrate compound with the agent for introducing a protecting group for a hydroxy group and/or a mercapto group according to claim 1 in a reaction.

15. The method according to claim 14, wherein the reaction is performed in coexistence of a base.

16. The method according to claim 15, wherein the reaction is performed by adding a base represented by the following formula (II)-1 or formula (II)-2:

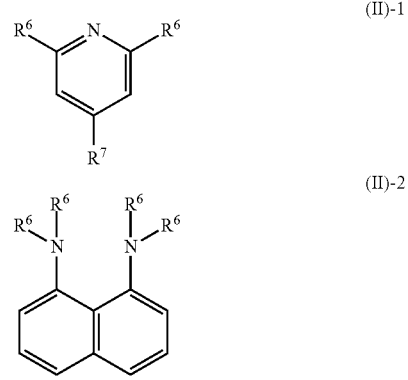

(II)-1

(II)-2 wherein each of $R^6$ and $R^7$ is independently a hydrogen atom or a linear or branched alkyl group having 1 to 5 carbon atoms.

* * * * *